United States Patent

Fink (10) Patent No.: US 12,373,682 B2
(45) Date of Patent: Jul. 29, 2025

(54) SENSOR QUALITY UPGRADE FRAMEWORK

(71) Applicant: Arizona Board of Regents on Behalf of the University of Arizona, Tucson, AZ (US)

(72) Inventor: Wolfgang Fink, Montrose, CA (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1349 days.

(21) Appl. No.: 16/142,914

(22) Filed: Sep. 26, 2018

(65) Prior Publication Data

US 2019/0095793 A1    Mar. 28, 2019

Related U.S. Application Data

(60) Provisional application No. 62/563,619, filed on Sep. 26, 2017.

(51) Int. Cl.
*G06N 3/08* (2023.01)
*A61B 5/00* (2006.01)
(Continued)

(52) U.S. Cl.
CPC ........... *G06N 3/08* (2013.01); *A61B 5/02438* (2013.01); *A61B 5/318* (2021.01); *A61B 5/7221* (2013.01);
(Continued)

(58) Field of Classification Search
CPC .......... G06N 3/0454; G06N 3/08; G06N 3/04; G06N 3/0445; G06N 20/00; G06N 3/084;
(Continued)

(56) References Cited

PUBLICATIONS

Vepakomma et al., A-Wristocracy: Deep Learning on Wrist-worn Sensing for Recognition of User Complex Activities, 2015 (Year: 2015).*

(Continued)

*Primary Examiner* — David Yi
*Assistant Examiner* — Charles C Kuo
(74) *Attorney, Agent, or Firm* — Thomas | Horstemeyer, LLP (57) ABSTRACT

Various examples related to upgrading low quality sensor output data in real time to provide high quality data suitable for, e.g., medical monitoring and diagnosis, or other non-medical analysis applications are presented. In one example, among others, a method includes training an artificial neural network (ANN) or learning logic based upon concurrent sensor output data from sensors to provide higher-quality sensor data from one of the sensors; obtaining subsequent sensor output data from the one sensor; and generating subsequent higher-quality sensor output data by applying the trained ANN or learning logic to the subsequent sensor output data. In another example, a device includes a sensor that generates higher-quality sensor output data using a trained ANN or learning logic. In another example, a system includes a mobile user device that receives low-quality sensor output data from a sensor and generates higher-quality sensor output data using a trained ANN or learning logic.

25 Claims, 4 Drawing Sheets

(51) Int. Cl.
*A61B 5/024* (2006.01)
*A61B 5/318* (2021.01)
*G06N 3/043* (2023.01)
*G16H 40/63* (2018.01)
*G16H 40/67* (2018.01)
*G16H 50/20* (2018.01)
*G16H 50/70* (2018.01)

(52) U.S. Cl.
CPC .......... *A61B 5/7264* (2013.01); *G06N 3/043* (2023.01); *G16H 40/63* (2018.01); *G16H 40/67* (2018.01); *G16H 50/20* (2018.01); *G16H 50/70* (2018.01); *A61B 5/0022* (2013.01); *A61B 5/02405* (2013.01); *A61B 5/681* (2013.01)

(58) Field of Classification Search
CPC ...... G06N 3/0472; G06N 3/063; G06N 7/005; G06N 3/0481; G06N 3/088; G06N 3/02; G06N 5/04; G06N 20/10; G06N 5/046; G06N 7/00; G06N 5/022
See application file for complete search history.

(56) References Cited

PUBLICATIONS

Rubel et al., Toward Personal eHealth in Cardiology. Results from the EPI-MEDICS TeleMedicine Project, 2005, Journal of Electrocardiology 38 (2005), pp. 100-106 (Year: 2005).*
Esposito et al., Dynamic Neural Network Architectures for On Field Stochastic Calibration of Indicative Low Cost Air Quality Sensing Systems, 2016, Sensors and Actuators B 231 (2016) 701-713 (Year: 2016).*
Xiong et al., ECG Signal Enhancement Based On Improved Denoising Auto-Encoder, 2016, Engineering Applications of Artificial Intelligence 52 (2016) 194-202 (Year: 2016).*
Autonomous self-configuration of artificial neural networks for data classification or system control by W. Fink (Proceedings of the SPIE, vol. 7331, id. 733105, May 2009).
Stochastic Optimization Framework (SOF) for Computer-Optimized Design, Engineering, and Performance of Multi-Dimensional Systems and Processes by W. Fink (Proceedings of the SPIE, vol. 6960, id. 69600N, Apr. 2008).

* cited by examiner

SENSOR QUALITY UPGRADE FRAMEWORK

CROSS REFERENCE TO RELATED APPLICATIONS

This application claims priority to, and the benefit of, U.S. provisional application entitled "Sensor Quality Upgrade Framework" having Ser. No. 62/563,619, filed Sep. 26, 2017, the entirety of which is hereby incorporated by reference.

BACKGROUND

Mobile Health (M-Health) is the intersection of mobile technology and healthcare. M-Health and Tele-Health are deeply intertwined and share the possibility of reshaping how and where healthcare is delivered. M-Health is an emerging field characterized by the use of portable, mobile devices capable of collecting, storing, retrieving, and transmitting data over wireless networks in real time for the purpose of improving safety and quality of care. Moreover, M-Health and Tele-Health harbor the potential of significant savings in healthcare costs to patients, health insurers, and economies at large.

The concept of M-Health centers on how to decentralize healthcare so that effective decisions can be made where patients are located. M-Health utilizes existing provider components in addition to its application in home Tele-Health systems. In Tele-Health systems mobile phones, PDAs, and wearable sensors with wired or wireless networking capabilities can serve as gateways that process, store, and transfer measured parameters to clinicians or cloud-based server backends for further analysis or diagnosis. Additionally, there is particular interest in how M-Health can improve access to care in developing countries (e.g., third world countries with developing economies). Many wearable sensors in healthcare (e.g., heart rate variability (HRV) sensors) do not deliver medical grade data, or data that are suitable, useful and accurate enough for subsequent or concurrent medical diagnoses. Because of this, there is a need for a framework that can potentially upgrade and/or enhance low quality sensor output for medical diagnosis and other applications.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various embodiments of methods, systems and devices related to upgrading low quality sensor output data in real time to provide high quality data suitable for, e.g., medical monitoring and diagnosis, or other analysis applications including, but not limited to, medical and non-medical applications. Reference will now be made in detail to the description of the embodiments as illustrated in the drawings, wherein like reference numbers indicate like parts throughout the several views.

Many wearable sensors in healthcare (e.g., heart rate variability (HRV) sensors) do not deliver medical grade data, or data that are useful and accurate enough for subsequent or concurrent medical diagnoses. Thus, much of the wearable sensor data are unusable for M-Health applications. In addition, the associated wearable sensor market (e.g., Fitbit®, Apple Watch, etc.) is exploding as well. The use of these devices has become part of the daily routine of their users. These devices can provide large amounts of additional data that, while not medical grade, can be used in subsequent or concurrent analyses. A sensor quality upgrade framework (SQUF) is disclosed that can be used to upgrade and/or enhance low quality sensor output data to medically or other, non-medical, useful data in real time. The improved data can be utilized for medical diagnoses for the benefit of patients or for other applications. Artificial neural networks, such as single- or multi-layer feedforward networks, single- or multi-layer perceptrons, single- or multi-layer recurrent neural networks, and/or Hopfield attractor networks can be used to upgrade and/or enhance the sensor output data. Other artificial neural networks, such as extreme learning machines (ELM), support vector machines (SVM), convolutional neural networks (CNN) and other known techniques in machine learning, deep learning, or artificial intelligence can be used as well. While the sensor quality upgrade framework (SQUF) is discussed here with respect to an example of M-Health applications, it is equally applicable to a wide variety of other applications including, but not limited to, non-medical applications that utilize sensors that provide low quality output signals. The following description is not intended to limit its applicability to other situations (e.g., geophysical and environmental sensors and systems).

Artificial neural networks (ANN), such as single- or multi-layered feedforward networks (e.g., single- or multi-layered perceptrons), extreme learning machines (ELM), support vector machines (SVM), convolutional neural networks (CNN), stochastic neural networks (SNN), probabilistic neural networks (PNN), single- or multi-layered recurrent networks, and/or fully connected attractor networks (e.g., Hopfield attractor networks), are at the core of machine learning, deep learning, artificial intelligence (AI), and cognizant computing systems. Other machine learning techniques comprise network-like modalities, such as fuzzy logic, and fuzzy cognitive maps, etc. Common to all the above and other techniques is that they can be trained, e.g., with stochastic optimization frameworks (SOF), backpropagation algorithms; backpropagation through time (BPTT) algorithms, real-time recurrent learning (RTRL) algorithms, Hebb rule algorithms; projection rule algorithms; or pseudoinverse algorithms. ANNs are powerful methods that can be used for, but are not limited to:

The classification and analysis of data (e.g., multi-dimensional data);
The learning of rules underlying data (e.g., for "generalization"); and
The control of dynamic, highly non-linear systems or linear systems.

Figure 1A:
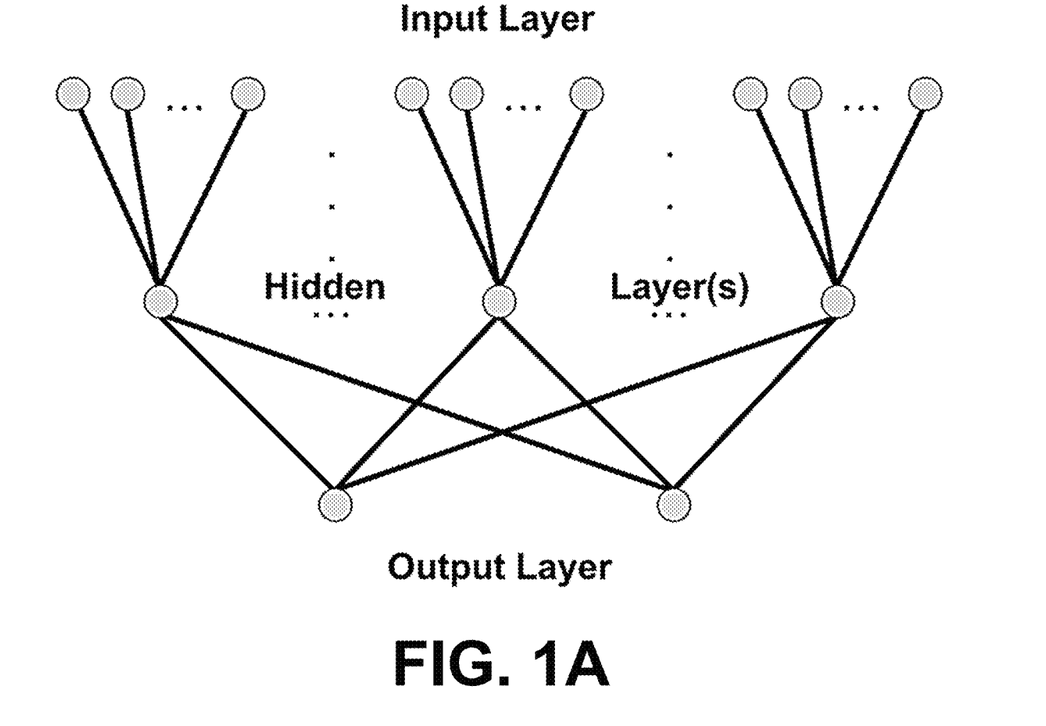
FIGS. 1A and 1B are examples of artificial neural networks (ANNs), in accordance with various embodiments of the present disclosure.
Figure 1B:
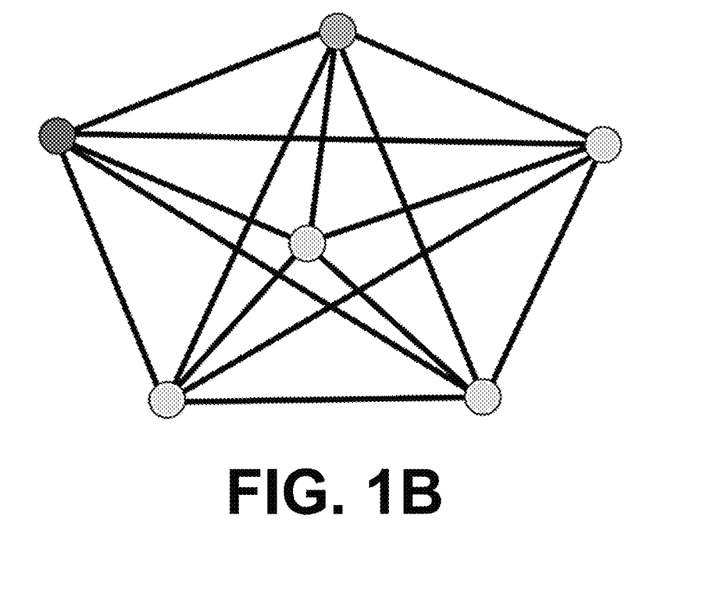

In general terms, ANNs comprise mathematical/computational neurons (e.g., McCulloch-Pitts neurons) that are binary or real-valued entities combined with, e.g., sigmoidal transfer functions (e.g., tan h(x)) to imitate the action potentials in biological neurons. Other transfer functions, such as, but not limited to, transfer functions based on physics, physics-based models, mathematics, mathematics-based models, or combinations thereof can be employed as well. These neurons can be assembled in layers in the case of feedforward networks, which are interconnected by real-valued or binary neural couplings or weights, which act as inputs to or outputs from respective neurons for the propagation of information, or can include cases where the neurons are interconnected and arranged according to a linked list rather than in layers. FIG. 1A illustrates an example of a tree-like feedforward multi-layer perceptron with a neural input layer, one or more hidden layers, and an output layer. In some instances (e.g., recurrent neural networks) at least some of the output neurons are connected via real-valued or binary neural couplings or weights to at least some of the input neurons. In the case of attractor networks, such as Hopfield attractor networks, the neurons are fully interconnected as a non-layered ensemble, acting both as input and output neurons that undergo a dynamic iteration process (e.g., dynamic relaxation process) to update their states. FIG. 1B illustrates an example of a fully connected Hopfield attractor network.

ANNs try imitating the processing of biological brains, and can be used for learning algorithms, knowledge discovery or creation, dynamic control, and in the development of cognizant computing architectures and systems. The classification and generalization capabilities of ANNs arise from the interconnection architecture and the coupling strengths. To perform a certain classification or control task with a particular ANN architecture (e.g., the number of neurons, number of layers, etc.), the inter-neuron couplings and their respective coupling strengths have to be determined by:

(1) A priori design; or
(2) By using training algorithms, such as, e.g., error backpropagation and test data. See, e.g., "Learning representations by back-propagating errors" by Rumelhart et al. (Nature 323 533-6, 1986) and "Learning internal representations by error propagation" by Rumelhart et al. (*Parallel Distributed Processing*, eds. D. E. Rumelhart and J. L. McClelland Cambridge: MIT Press (1986)).

In the disclosed SQUF, an ANN can be trained on a combination of at least one time series of data produced by a variety of one or more sensors including at least one low-quality wearable sensor, whose data quality is to be upgraded/enhanced, as well as at least one concurrent time series of data produced by at least one high-quality, "gold-standard" and/or ground-truth sensor such as, e.g., a clinical-grade, wearable or non-wearable/immobile, or highly expensive sensor or machine. For example, error backpropagation, or other deterministic and non-deterministic ANN training algorithms can be used to train the ANN to reduce or minimize the error between the at least one time series produced by the at least one wearable "low-quality" sensor and the at least one concurrent time series produced by the at least one gold-standard/ground-truth sensor or machine.

However, backpropagation and other algorithms can only be used to train ANNs where the architecture is known, given, or predetermined. For example, a backpropagation algorithm; gradient learning algorithm; or perceptron learning rule algorithm can be used for training feedforward networks; and a Hebb rule algorithm; projection rule algorithm; or pseudoinverse algorithm can be used for training Hopfield attractor networks. For training of recurrent neural networks, backpropagation through time (BPTT) or real-time recurrent learning (RTRL) algorithms can be used, for example. In particular a stochastic optimization framework can be employed to determine the architecture of at least one ANN and train the at least one ANN to minimize the error between the at least one time series produced by the at least one wearable sensor and the at least one concurrent time series produced by the at least one gold-standard/ground-truth sensor or machine. A more extensive discussion of SOF applied to the determination of ANN architectures and training thereof is provided by "Autonomous self-configuration of artificial neural networks for data classification or system control" by W. Fink (Proc. SPIE, Vol. 7331, 733105 (2009); DOI:10.1117/12.821836), which is hereby incorporated by reference in its entirety.

Figure 2:
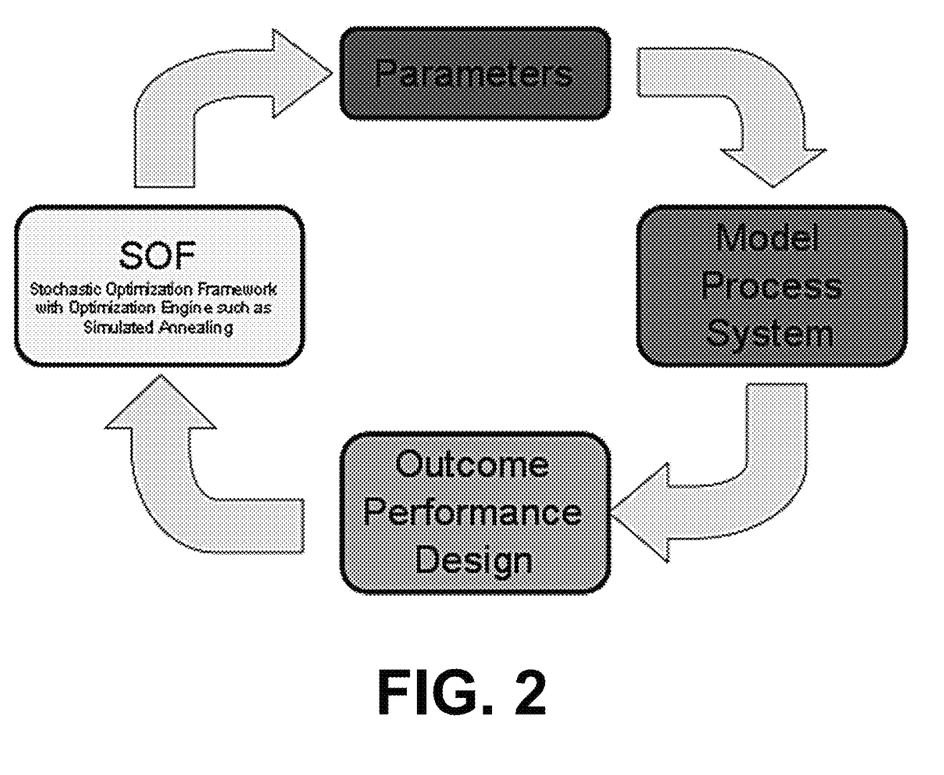
FIG. 2 is a schematic diagram illustrating an example of functional flow of a stochastic optimization framework (SOF), in accordance with various embodiments of the present disclosure.

FIG. 2 is a schematic diagram illustrating the functional flow of the SOF. In particular, SOF allows for efficient sampling of the entire ANN-intrinsic coupling space (1) by repeatedly executing the given classification task by the SOF-configured ANN (e.g., ANN architecture and/or associated coupling strengths), and (2) by comparing the outcomes against the desired outcome to minimize the error (e.g., RMSE, or single maximum occurring error, etc.) between the at least one time series produced by the at least one wearable sensor and the at least one concurrent time series produced by the at least one gold-standard/ground-truth sensor/machine, which results in a fitness measure. The goal of the SOF is to optimize this fitness, e.g., by minimizing the error. A more extensive discussion of SOF is provided by "Stochastic optimization framework (SOF) for computer-optimized design, engineering, and performance of multi-dimensional systems and processes" by W. Fink (Proc. SPIE, Vol. 6960, 2008), which is hereby incorporated by reference in its entirety.

Figure 3:
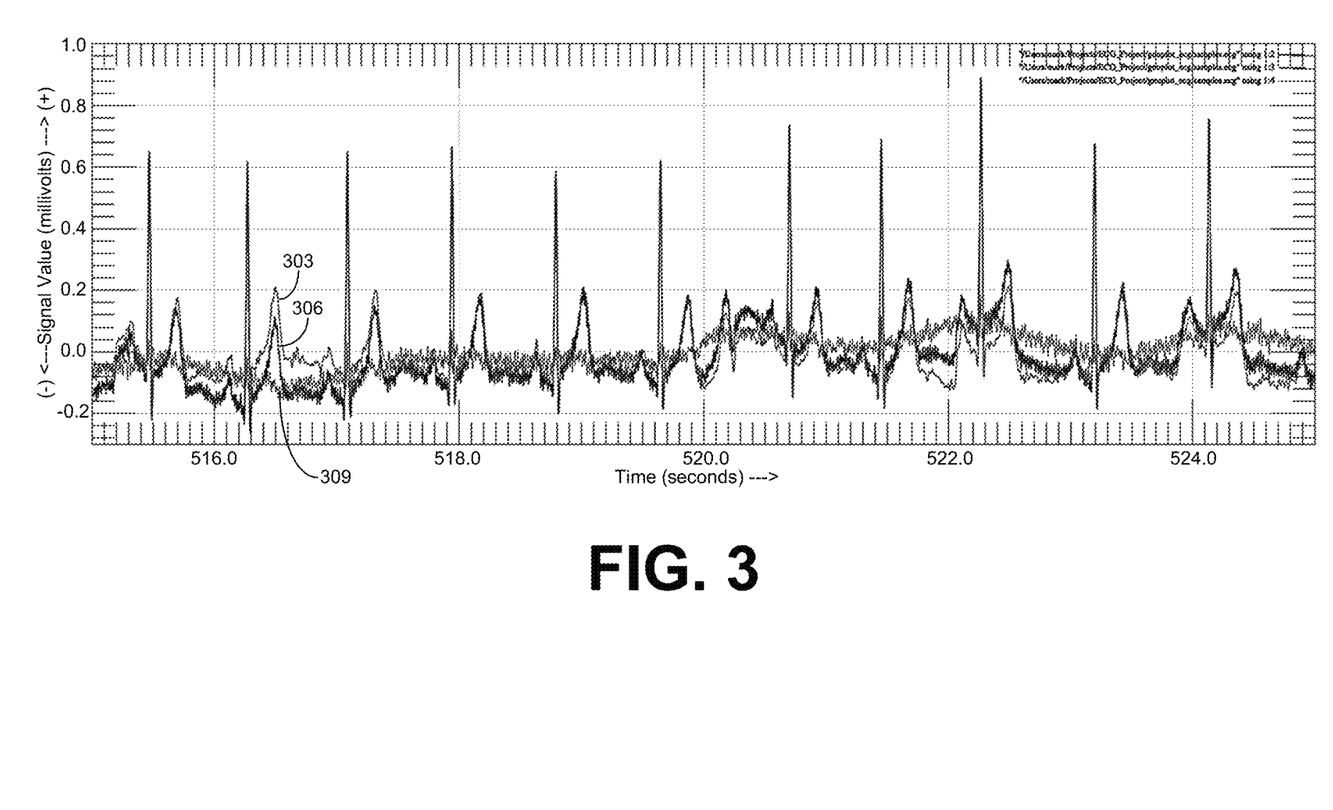
FIG. 3 is a plot illustrating an example of ECG data generated by a low-quality wearable sensor and by a gold-standard/ground-truth sensor/machine, and the error, i.e., the difference between the two data sets, in accordance with various embodiments of the present disclosure.

FIG. 3 shows an example of ECG data generated by a gold-standard/ground-truth sensor/machine (curve 303) and by a low-quality wearable sensor (curve 306). Curve 309 denotes the error between the two concurrent time series. It is this error 309 that the SOF optimizes, e.g., by minimizing it to within a (user-)defined level or threshold. The error minimization through the use of, e.g., the SOF-configured ANN, can work both in the amplitude domain (e.g., along the y-axis of FIG. 3) as well as in the time domain (e.g., along the x/t-axis of FIG. 3), or in both domains simultaneously. Other domains, such as, e.g., the Fourier domain, are applicable as well.

Once the ANN has been trained, it will have learned the specific deviation characteristics of the at least one low-quality wearable sensor being upgraded and/or enhanced with regard to the output of the at least one gold-standard/ground-truth sensor or machine. The generalization ability of this particular sensor-specific ANN can now be exploited to upgrade/enhance the quality of all forthcoming new (or subsequent) time series of data generated by the at least one low-quality wearable sensor to the level of (or close to the level of) the at least one gold-standard/ground-truth sensor/machine by passing these time series of data through the sensor-specific ANN. In other words, curve 306 becomes more similar or identical to curve 303 in FIG. 3. As an example, quality correction/upgrade/improvement via the sensor-specific ANN in the time domain of the ECG data generated by a low-quality wearable sensor may result in more accurate HRV-data, closely matching the data that would be concurrently generated by the gold-standard/ ground-truth sensor or machine, which can be much more expensive and/or immobile. In one instantiation, a gold-standard or ground-truth sensor or machine can be understood as the best commercially available sensor or machine, generating highest quality data, where highest quality can be defined as, e.g., at least one of highest sampling frequency/ rate, highest spatial resolution, highest data accuracy or fidelity, etc. The above-detailed sensor quality upgrade can be further enhanced, refined, or reconfigured after operation begins by comparing the upgraded or enhanced output data with subsequently obtained gold-standard/ground-truth sensor or machine data, or with data from other monitoring sensors worn by the patient (or user) to further reduce the error. SOF can be used to further optimize or reduce the error as more data are obtained during operation. This can also account for and mitigate, or even eliminate, sensor drift or shift over time.

The sensor quality upgrade framework (SQUF) can be implemented by at least one computing device(s) that is configured to receive data from at least one low-quality sensor such as, e.g., a wearable sensor that can monitor health information of a patient or user wearing the device. Initially, high-quality data (e.g., medically useful data) received from at least one gold-standard/ground-truth sensor or machine and concurrent output data received from the corresponding at least one low-quality sensor can be used to train at least one ANN. SOF can be used to execute, enable, and/or accelerate the training and improve the quality of the low-quality sensor output data. After training is complete, the SOF-configured ANN can be used to improve data received from the low-quality sensor in real time. In some cases, the low-quality sensor data can be communicated via a mobile user device (e.g., a smart phone) that is linked with the sensor. The low-quality sensor data can be upgraded in (near) real time on, e.g., the sensor, the mobile user device, or on a server backend via the cloud or Internet. The SOF-configured ANN can be communicated to the mobile user device and/or sensor from the at least one computing device after training. If the sensor data are upgraded on the sensor or the mobile user device, the upgraded data can be communicated to the server backend via the mobile user device or directly from the sensor.

The SQUF can operate in a variety of configurations. For example, the trained ANN can operate on the sensor directly and transform low-quality raw sensor output data into upgraded (higher-quality) output data, which can then be sent either directly or via the mobile user device to a computing device, such as, e.g., a remotely located computing device, server backend or other mobile user device for evaluation. In another implementation, the ANN can operate on the mobile user device (e.g., a smartphone) that is linked (or communicatively coupled) to the sensor. Here, the low-quality sensor data can be communicated to the mobile user device, which then applies the trained ANN to generate the higher-quality sensor data. The high-quality data can be sent to, e.g., a computing device (e.g., a server backend) or another mobile user device for evaluation. In a third implementation, the trained ANN operates on the computing device (e.g., a remotely located and/or cloud-based server backend) that gets the low-quality sensor data either directly from the sensor, or via a mobile user device linked to the sensor. The computing device can analyze the upgraded data itself, or communicate the higher-quality sensor data to another computing device, or mobile user device, for evaluation. In some cases, the SOF training of the ANN can also occur on the sensor, mobile user device, or computing device (e.g., a remotely located and/or cloud-based sensor).

The upgraded (higher-quality) sensor data can be utilized by other applications monitoring the patient or user, or can be transmitted to a server backend (e.g., via the cloud or Internet) or other computing device for automated analysis and/or to a user device (e.g., via the cloud or Internet) that allows a physician or other healthcare professional to evaluate the information. The ability to improve the data quality in real time makes it possible to provide low-cost, low-quality sensors to more patients and/or third world countries, or people who live in geographically dispersed/remote areas, or who operate in austere/extreme environments such as the arctic, the military theatre, space, natural disaster stricken areas, etc. SQUF can potentially benefit many areas of healthcare, e.g., ranging from pediatric to elderly healthcare, emergency to outpatient (ambulatory) care, and bedside to ICU (intensive care unit)-based patient care, because of the plethora of sensors involved, and, more so in the future, because of the Internet of Things (IoT). As examples of non-medical applications, SQUF can potentially benefit areas in the $4^{th}$ industrial revolution (i.e., industry 4.0), such as, but not limited to, smart manufacturing, advanced manufacturing, prognostics and health management (PHM), etc.—all areas that utilize and are heavily dependent on large numbers of deployed sensors.

Figure 4:
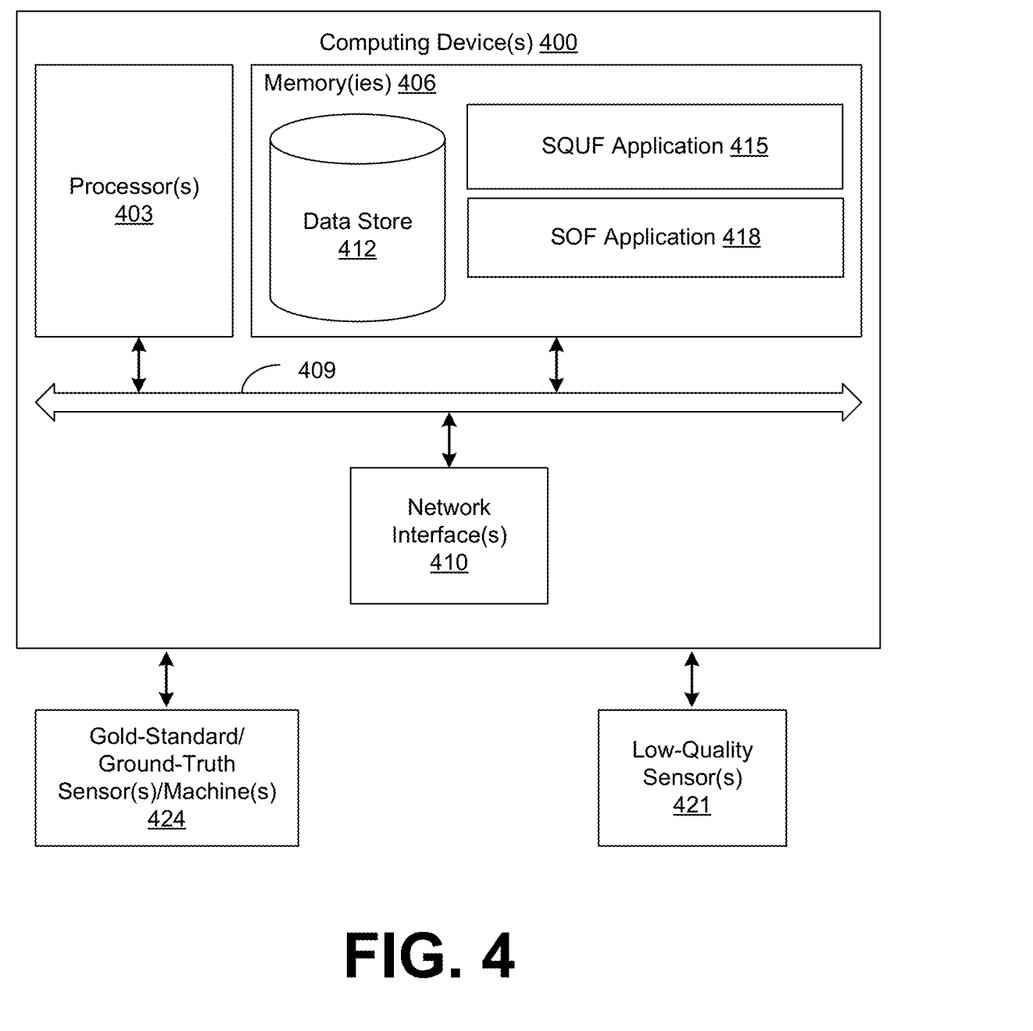
FIG. 4 is a schematic diagram illustrating an example of a computing system for implementing the sensor quality upgrade framework (SQUF), in accordance with various embodiments of the present disclosure.

With reference to FIG. 4, shown is a schematic block diagram of a computing device 400. In some embodiments, among others, the computing device 400 may represent a mobile device (e.g., a smartphone, tablet, computer, VR-, AR- and MR-glasses (i.e., virtual, augmented or mixed reality, respectively) or HMDs (i.e., head mounted displays), etc.). Each computing device 400 includes at least one processor circuit, for example, having a processor 403 and a memory 406, both of which are coupled to a local interface 409. To this end, each computing device 400 may comprise, for example, at least one server computer or like device, which can be utilized in a cloud based environment. The local interface 409 may comprise, for example, a data bus with an accompanying address/control bus or other bus structure as can be appreciated.

In some embodiments, the computing device 400 can include one or more network interfaces 410. The network interface 410 may comprise, for example, a wireless transmitter, a wireless transceiver, and/or a wireless receiver (e.g., Bluetooth®, Wi-Fi, Ethernet radio modem, etc.), or an appropriate wired interface (e.g., Ethernet, etc.) or communications circuitry. As discussed above, the network interface 410 can communicate to a remote computing device using an appropriate communications protocol. As one skilled in the art can appreciate, other wireless protocols may be used in the various embodiments of the present disclosure. In addition, the computing device 400 can be in communication with one or more low-quality sensor(s) 421 and/or one or more gold-standard/ground-truth sensor(s)/ machine(s) 424.

Stored in the memory 406 are both data and several components that are executable by the processor 403. In particular, stored in the memory 406 and executable by the processor 403 are at least one sensor quality upgrade framework (SQUF) application 415, at least one stochastic optimization framework (SOF) application 418, and potentially other applications. Also stored in the memory 406 may be a data store 412 and other data. In addition, an operating system may be stored in the memory 406 and executable by the processor 403.

It is understood that there may be other applications that are stored in the memory 406 and are executable by the processor 403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, assembler, Matlab® (compiled), or other programming languages.

A number of software components are stored in the memory 406 and are executable by the processor 403. In this respect, the term "executable" means a program or application file that is in a form that can ultimately be run by the processor 403. Examples of executable programs may be, for example, a compiled program that can be translated into machine code in a format that can be loaded into a random access portion of the memory 406 and run by the processor 403, source code that may be expressed in proper format such as object code that is capable of being loaded into a random access portion of the memory 406 and executed by the processor 403, or source code that may be interpreted by another executable program to generate instructions in a random access portion of the memory 406 to be executed by the processor 403, etc. An executable program may be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 403 may represent multiple processors 403 and/or multiple processor cores and the memory 406 may represent multiple memories 406 that operate in parallel processing circuits, respectively, such as multicore systems, FPGAs, GPUs, GPGPUs, spatially distributed computing systems (e.g., connected via the cloud and/or Internet). In such a case, the local interface 409 may be an appropriate network that facilitates communication between any two of the multiple processors 403, between any processor 403 and any of the memories 406, or between any two of the memories 406, etc. The local interface 409 may comprise additional systems designed to coordinate this communication, including, for example, performing load balancing. The processor 403 may be of electrical or of some other available construction.

Although the SQUF application 415 and the SOF application 418, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

Also, any logic or application described herein, including the SQUF application 415 and the SOF application 418, that comprises software or code can be embodied in any non-transitory computer-readable medium for use by or in connection with an instruction execution system such as, for example, a processor 403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, optical discs, optical storage, holographic storage, data crystals, or holographic data crystals. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the SQUF application 415 and the SOF application 418, may be implemented and structured in a variety of ways. For example, one or more applications described may be implemented as modules or components of a single application. Further, one or more applications described herein may be executed in shared or separate computing devices or a combination thereof (e.g., parallel processing). For example, a plurality of the applications described herein may execute in the same computing device 400 (e.g., multi-tasking), or in multiple computing devices in the same computing environment. Additionally, it is understood that terms such as "application," "service," "system," "engine," "module," and so on may be interchangeable and are not intended to be limiting.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A method for upgrading sensor output quality, comprising:
   training, by a computing device, an artificial neural network (ANN) based upon time series of sensor output data from a first sensor and concurrent time series of output data received from a second sensor, where the time series of sensor output data from the first sensor is input to the ANN during training and the concurrent time series of output data from the second sensor is a corresponding higher-quality version of the time series of sensor output data from the first sensor, the training configured to reduce an error between the time series of sensor output data of the first sensor passed through the ANN and the concurrent time series of output data from the second sensor, thereby providing a trained ANN configured to provide corresponding higher-quality time series sensor data when applied to additional time series of sensor output data from the first sensor;
   obtaining subsequent time series of sensor output data from the first sensor, the subsequent time series of sensor output data obtained after training the ANN; and
   generating corresponding subsequent higher-quality time series of sensor output data by applying the trained ANN to the subsequent time series of sensor output data from the first sensor.

2. The method of claim 1, wherein the first sensor is a low-quality sensor and the second sensor is a gold-standard or ground-truth sensor.

3. The method of claim 1, wherein the first sensor is worn by a user.

4. The method of claim 1, comprising communicating the corresponding subsequent higher-quality time series of sensor output data to a mobile user device for evaluation by a physician or healthcare professional.

5. The method of claim 1, comprising communicating the corresponding subsequent higher-quality time series of sensor output data to a server backend for automated evaluation.

6. The method of claim 1, wherein the training of the ANN is implemented using a stochastic optimization framework (SOF).

7. The method of claim 1, wherein the training of the ANN is implemented using at least one of:
   a backpropagation algorithm;
   a gradient learning algorithm;
   a perceptron learning rule algorithm;
   a Hebb rule algorithm;
   a projection rule algorithm; or
   a pseudoinverse algorithm.

8. The method of claim 1, wherein the subsequent time series of sensor output data or the corresponding subsequent higher-quality time series of sensor output data are provided directly to the computing device from the first sensor.

9. The method of claim 1, wherein the trained ANN is communicated to the first sensor for processing of the subsequent time series of sensor output data.

10. The method of claim 1, wherein the corresponding subsequent higher-quality time series of sensor output data are produced by the first sensor or by a server backend.

11. The method of claim 1, wherein the subsequent time series of sensor output data or the corresponding subsequent higher-quality time series of sensor output data are provided to the computing device via a mobile user device communicatively coupled to the first sensor.

12. The method of claim 11, wherein the trained ANN is communicated to the mobile user device for processing of the subsequent time series of sensor output data.

13. The method of claim 11, wherein the corresponding subsequent higher-quality time series of sensor output data are produced by the mobile user device.

14. The method of claim 13, wherein the corresponding subsequent higher-quality time series of sensor output data produced by the mobile user device are communicated to a physician or healthcare professional.

15. The method of claim 1, wherein the ANN comprises at least one of:
   a single layer perceptron;
   a multi-layer perceptron;
   a Hopfield attractor network;
   a single-layer recurrent neural network; or
   a multi-layer recurrent neural network.

16. A method for upgrading sensor output quality, comprising:
   training, by a computing device, a learning logic based upon time series of sensor output data from a first sensor and concurrent time series of output data received from a second sensor, where the time series of sensor output data from the first sensor is input to the learning logic during training and the concurrent time series of output data from the second sensor is a corresponding higher-quality version of the time series of sensor output data from the first sensor, the learning logic comprising at least one of deep learning, artificial intelligence, fuzzy logic, or fuzzy cognitive map, the training configured to reduce an error between the time series of sensor output data of the first sensor passed through the learning logic and the concurrent time series of output data from the second sensor, thereby providing a trained learning logic configured to provide corresponding higher-quality time series of sensor data when applied to additional time series of sensor output data from the first sensor;

obtaining subsequent time series of sensor output data from the first sensor, the subsequent time series of sensor output data obtained after training the learning logic; and generating corresponding subsequent higher-quality time series of sensor output data by applying the trained learning logic to the subsequent time series of sensor output data.

17. A device for upgrading sensor output quality, comprising:
a first sensor comprising at least one of an artificial neural network (ANN) or learning logic trained to reduce an error between an output of the at least one of the ANN or learning logic when applied to time series of sensor output data from the first sensor and concurrent time series of output data from a second sensor, where the concurrent time series of output data from the second sensor is a corresponding higher-quality version of the time series of sensor output data from the first sensor, the first sensor configured to:
obtain low-quality time series of sensor output data;
generate corresponding higher-quality time series of sensor output data by applying the at least one of the trained ANN or learning logic to the low-quality time series of sensor output data; and
communicate the corresponding higher-quality time series of sensor output data to a remotely located computing device.

18. The device of claim 17, wherein the first sensor is worn by a user.

19. The device of claim 17, wherein the corresponding higher-quality time series of sensor output data are communicated to the remotely located computing device via a mobile user device communicatively coupled to the first sensor.

20. The device of claim 17, wherein the ANN comprises at least one of:
a single layer perceptron;
a multi-layer perceptron;
a Hopfield attractor network;
a single-layer recurrent neural network; or
a multi-layer recurrent neural network.

21. The device of claim 17, wherein the learning logic comprises at least one of deep learning, artificial intelligence, fuzzy logic, or fuzzy cognitive map.

22. A system for upgrading sensor output quality, comprising:
a first sensor configured to obtain time series of sensor output data;
a mobile user device communicatively coupled to the first sensor, the mobile user device comprising at least one of an artificial neural network (ANN) or learning logic trained to reduce an error between an output of the ANN or learning logic when applied to the time series of sensor output data of the first sensor and concurrent time series of output data from a second sensor, where the concurrent time series of output data from the second sensor is a corresponding higher-quality version of the time series of sensor output data from the first sensor, the mobile user device configured to:
receive low-quality time series of sensor output data from the first sensor;
generate corresponding higher-quality time series of sensor output data by applying the at least one of the trained ANN or learning logic to the low-quality time series of sensor output data; and
communicate the corresponding higher-quality time series of sensor output data to a remotely located computing device.

23. The system of claim 22, wherein the first sensor is worn by a user.

24. The system of claim 22, wherein the ANN comprises at least one of:
a single layer perceptron;
a multi-layer perceptron;
a Hopfield attractor network;
a single-layer recurrent neural network; or
a multi-layer recurrent neural network.

25. The system of claim 22, wherein the learning logic comprises at least one of deep learning, artificial intelligence, fuzzy logic, or fuzzy cognitive map.

* * * * *